(12) United States Patent
Montgomery

(10) Patent No.: US 7,566,299 B2
(45) Date of Patent: Jul. 28, 2009

(54) PENIS ENLARGEMENT DEVICE

(76) Inventor: Jim Montgomery, 2802 Old Highway Rd., Morgan, UT (US) 84050

(*) Notice: Subject to any disclaimer, the term of this patent is extended or adjusted under 35 U.S.C. 154(b) by 581 days.

(21) Appl. No.: 11/259,366

(22) Filed: Oct. 25, 2005

(65) Prior Publication Data

US 2006/0243283 A1 Nov. 2, 2006

Related U.S. Application Data

(60) Provisional application No. 60/622,122, filed on Oct. 25, 2004.

(51) Int. Cl.
*A61F 5/00* (2006.01)
(52) U.S. Cl. ........................................................ 600/38
(58) Field of Classification Search ............. 600/38–41; 128/897, 898
See application file for complete search history.

(56) References Cited

U.S. PATENT DOCUMENTS

| | | | |
|---|---|---|---|
| 2,608,409 A * | 8/1952 | Pinkerton | 473/256 |
| 3,647,220 A * | 3/1972 | Burkart et al. | 473/238 |
| 3,716,239 A * | 2/1973 | Goudreau | 473/256 |
| 5,344,396 A | 9/1994 | Clark, Jr. | |
| 5,472,399 A | 12/1995 | Szekely | |
| D375,358 S | 11/1996 | Clark | |
| 5,599,275 A | 2/1997 | France | |
| 5,707,341 A | 1/1998 | Mathewuse | |
| 6,173,714 B1 | 1/2001 | Cho | |
| 6,416,460 B1 | 7/2002 | Jochum | |
| 6,582,356 B2 | 6/2003 | Kim | |

* cited by examiner

*Primary Examiner*—Samuel G Gilbert
(74) *Attorney, Agent, or Firm*—Thorpe North & Western LLP

(57) ABSTRACT

A penis enlargement device including (a) an end ring configured to be inserted onto the shaft of a penis and to be positioned proximate the head of the penis, wherein the end ring includes a weighted mass having a front edge, a back mating edge, an outer sidewall extending between the front and back edges, and an inner sidewall also extending between the front and back edges and having, at least in part, a nonlinear variable diameter segment configured to position the back mating edge above the shaft; (b) a stealth ring also configured to be inserted onto the shaft of the penis adjacent the end ring, wherein the stealth ring includes a weighted mass having a front mating edge configured to interface with the back mating edge of the end ring, a back mating edge configured to interface with a second stealth ring, an outer sidewall of constant diameter and extending between the front and back mating edges, and an inner sidewall also extending between the front and back mating edges and having, at least in part, a nonlinear variable diameter configured to position the front and back mating edges above the shaft, and wherein the end ring and the stealth ring interact to form a volume of space upon being positioned adjacent one another, which volume of space is configured to receive the skin of the penis to reduce the likelihood of pinching upon placing and positioning the end and stealth rings about the shaft of the penis, as well as during a penis enlargement session.

16 Claims, 6 Drawing Sheets

PENIS ENLARGEMENT DEVICE

RELATED APPLICATIONS

This application claims priority to U.S. Provisional Patent Application Ser. No. 60/622,122, filed Oct. 25, 2004, and entitled, "Penis Enlargement Device," which is incorporated by reference in its entirety herein.

FIELD OF THE INVENTION

The present invention relates generally to methods and devices for enhancing the penis of a male individual, and more particularly to a variable, non-mechanical and non-invasive penis enlargement device configured to provide permanent enlargement of the penis over a period of time.

BACKGROUND OF THE INVENTION AND RELATED ART

Like any other feature of the human body, there are variations in the natural size, shape, and overall physiological characteristics of the penis between individuals. Ostensibly, the characteristic of most concern to many individuals, and one of frequent debate, is the size of their penis. Indeed, it is well known that in some cases, natural penis size can vary significantly, but it is said that most individuals in the population are of average size.

Genetics play the primary role, in most cases, in determining natural penis size. However, there are those individuals that are victims of unfortunate circumstance, such as those that experience some type of abnormal growth that may be attributed to or a result of complications experienced during their development, resulting in a penis size that is, in some cases, much smaller than average.

While most individuals are content with their natural size, there are others that desire to increase the size of their penis. As a result, there has recently been several methods, devices, and systems that have surfaced that are designed and configured to enhance or enlarge the penis of an individual. Enlargement of the penis typically means increasing either the overall length of the penis, or increasing the girth or circumference of the penis, or both of these. The standard measurement for determining the length of the penis is typically from the pubis region to the tip of the penis, either during an erect or flaccid state.

Generally speaking, there are categorically two primary approaches that may be taken to enlarge the penis. The first approach is a non-invasive approach that focuses on enlargement of the penis over time, or prolonged penis enlargement, wherein the individual utilizes, on a periodic basis, some type of system or device and a corresponding and intended method to carry out the goals of either lengthening the penis, or increasing the overall girth of the penis, or both.

The second approach to penis enlargement is an invasive approach, wherein the user elects to undergo one or more developed surgical procedures, such as to receive implants. This second or surgical approach is considered to be outside the scope of the present invention, and is therefore, not discussed at length herein. Basically, however, surgery typically requires a derma fat transplant, or the injection of fat, from another part of the body, to enlarge the girth of the penis, followed by the incision of a suspensor ligament to increase the overall length of the penis. Such procedures run the same risks attendant to all surgical procedures, namely, the possibility of infection, complications, and adverse reactions to administered drugs or anesthesia. Furthermore, the effects of such procedures, if effective at all, are often only temporary, thus leaving the patient in the same pre-surgery circumstance.

Many people believe that by undergoing some type of non-invasive, prolonged penis enlargement practice is healthy. Claims have been made that by "exercising" the penis using a penis enlargement procedure, veins will become more prominent, the potential for an erectile dysfunction is decreased, circulation is improved, erections are more pronounced and last longer, etc.

Some of the more crude types of penis enlargement include: Jelging, which is a manual hand exercise that stretches the penis by trapping blood and forcing engorgement by way of a stroking motion; Uli, which is a technique utilizing a clamp that is applied to the base of the penis to trap blood in the corpora cavemosa to create a pressure that stretches the penis; v-stretch, which is a manual technique of stretching the penis over the arm of the individual; and Fower, which is a technique where the penis is pulled up under the buttocks and sat on for the purpose of stretching. These all have significant drawbacks and can often be dangerous to perform, especially over time.

One of the more popular penis enlargement techniques known is referred to as "hanging." Hanging is probably the most used penis enlargement technique and, for length gains, is perhaps the most efficient. Significant growth results can be achieved by a properly implemented hanging regimen. This has been recognized by many, including urologists specializing in penis lengthening procedures, many of whom insist their patients hang some type of weight from their penis to improve on surgical gains.

The concept of hanging is simple, namely using weights attached to a device coupled to the penis over a prolonged period of time for the purpose of stretching the penis, thus increasing its overall length. Over time, the penis is progressively stretched to achieve a permanent increase in length. While there currently exists several types of hanging devices and/or systems on the market, many of these devices are problematic, and can even be dangerous. Indeed, many of the devices used are anchored to the skin, or worse, to the glans portion of the penis, which contains delicate nerve bundles. Those hanging devices that are safe and that provide the best results are anchored to non-delicate structural areas of the penis shaft and progressively stretch these, as well as the ligaments present within the penis.

A variation of hanging is the concept of using weights directly on the penis. These are typically in the form of one or more weighted rings inserted onto the shaft of the penis. Essentially, the penis is passed through the aperture of one or more weighted rings, wherein the rings are secured in place by some type of soft material wrapped around the penis to prevent the rings from falling off. As there are no prior art rings specifically designed for penis enlargement, users have resigned to using what are the equivalent of golf weights. These golf weights comprise a plastic covered metal ring having a donut shape and are utilized by the golf industry as a swing weight to strengthen wrist muscles. Because of their convenient size, these golf weights have been adapted for use as penis enlargement devices. Typical golf weights have a 1¼ inch inside diameter that accommodates most penis sizes. However, because they were not developed for use as penis enlargement devices, these weights have several inherent deficiencies when applied to the practice of penis enlargement. First, they are rather light in weight while being bulky, thus providing only moderate results. The typical golf weight weighs only 5.35 ounces and comprises a thickness of about ½ to ⅜ of an inch. Thus, it is difficult to achieve significant results as it is impossible to obtain a collective weight necessary to achieve these results. Second, the golf weights comprise a donut shape, which results in a low contact point when stacked or positioned adjacent one another. This low contact point, namely the median of the outer sidewall, facilitates pinching of the skin of the penis during movement or if not positioned carefully. Third, it is difficult to conceal their presence when in use. Indeed, because of their shape, they are difficult to disguise or hide under clothing, and therefore, must be used in private settings to avoid embarrassment. Fourth, the donut shape causes a natural entrapment of the wrap used to secure the rings in place on the penis. The wrap will have a tendency to bundle up between the rings and the penis shaft, which limits the wear time before maintenance or adjustment is required.

SUMMARY OF THE INVENTION

In light of the problems and deficiencies inherent in the prior art, the present invention seeks to overcome these by providing a variable, non-mechanical and non-invasive penis enlargement device configured to provide permanent enlargement of the penis over a period of time.

In accordance with the invention as embodied and broadly described herein, the present invention features a penis enlargement device comprising, in one exemplary embodiment, (a) an end ring configured to be inserted onto a shaft of a penis and to be positioned proximate a head of the penis, the end ring comprising a weighted mass to effectuate stretching of the penis, and a non-uniform outside diameter to facilitate concealment thereof when being worn; (b) a stealth ring also configured to be inserted onto the shaft of the penis to be positioned aft of and adjacent the end ring, the end ring and the stealth ring forming a volume of space therebetween upon being positioned adjacent one another, the volume of space being configured to receive the skin of the penis, thereby reducing the likelihood of pinching the skin upon positioning the end and stealth rings about the shaft of the penis.

The present invention also features a penis enlargement device comprising: (a) an end ring configured to be inserted onto a shaft of a penis and to be positioned proximate a head of the penis, the end ring comprising a weighted mass, a front edge configured to be located against the shaft, a back edge supported above the shaft by an inner sidewall extending between the front edge and the back edge, the inner sidewall having, at least in part, a nonlinear variable diameter segment, and an outer sidewall extending between the front edge and the back edge; and (b) a first stealth ring also configured to be inserted onto the shaft of the penis adjacent the end ring, the stealth ring comprising a weighted mass, a front edge configured to interface with the back edge of the end ring, a back edge configured to interface with a second stealth ring, an outer sidewall extending between the front and back edges, and an inner sidewall also extending between the front and back edges and having, at least in part, a nonlinear variable diameter configured to locate the front and back edges proximate the outer sidewall and above the shaft, the inner sidewall of the end ring and the inner sidewall of the stealth ring defining a volume of space capable of receiving the skin of the shaft of the penis to reduce the likelihood of pinching upon positioning the stealth ring adjacent the end ring.

The present invention further features a method for lengthening and enlarging a penis of a human male, the method comprising: (a) inserting an end ring onto a shaft of the penis, the end ring comprising a weighted mass, a front edge, a back edge, an outer sidewall extending between the back and front edges in an inwardly tapering manner to help conceal the end ring, and an inner sidewall also extending between the front and back edges; (b) positioning the end ring proximate a head of the penis, the end ring being configured to stretch the penis under gravity; (c) securing the end ring in position on the shaft of the penis; and (d) wearing the end ring periodically for a duration of time to effectuate enlargement of the penis.

The method further comprises inserting a stealth ring onto the shaft of the penis prior to inserting the end ring, wherein the stealth ring is positioned adjacent the end ring and is configured to facilitate its concealment when being worn. A plurality of stealth rings may be worn in connection with the end ring.

BRIEF DESCRIPTION OF THE DRAWINGS

The present invention will become more fully apparent from the following description and appended claims, taken in conjunction with the accompanying drawings. Understanding that these drawings merely depict exemplary embodiments of the present invention they are, therefore, not to be considered limiting of its scope. It will be readily appreciated that the components of the present invention, as generally described and illustrated in the figures herein, could be arranged and designed in a wide variety of different configurations. Nonetheless, the invention will be described and explained with additional specificity and detail through the use of the accompanying drawings in which:

DETAILED DESCRIPTION OF EXEMPLARY EMBODIMENTS

The following detailed description of exemplary embodiments of the invention makes reference to the accompanying drawings, which form a part hereof and in which are shown, by way of illustration, exemplary embodiments in which the invention may be practiced. While these exemplary embodiments are described in sufficient detail to enable those skilled in the art practice the invention, it should be understood that other embodiments may be realized and that various changes to the invention may be made without departing from the spirit and scope of the present invention. Thus, the following more detailed description of the embodiments of the present invention, as represented in FIGS. 1 through 8, is not intended to limit the scope of the invention, as claimed, but is presented for purposes of illustration only and not limitation to describe the features and characteristics of the present invention, to set forth the best mode of operation of the invention, and to sufficiently enable one skilled in the art to practice the invention. Accordingly, the scope of the present invention is to be defined solely by the appended claims.

The following detailed description and exemplary embodiments of the invention will be best understood by reference to the accompanying drawings, wherein the elements and features of the invention are designated by numerals throughout.

The present invention features and describes a method and device for enlarging the penis of an individual using a variable, non-mechanical and non-invasive penis enlargement device that fits over and is supported on the shaft of the penis, is designed for extended wear, and is configured to stretch the skin, ligaments, and other non-delicate physiological structures of the penis for the purpose of providing permanent elongation or enlargement of the penis over a period of time.

Figure 1:
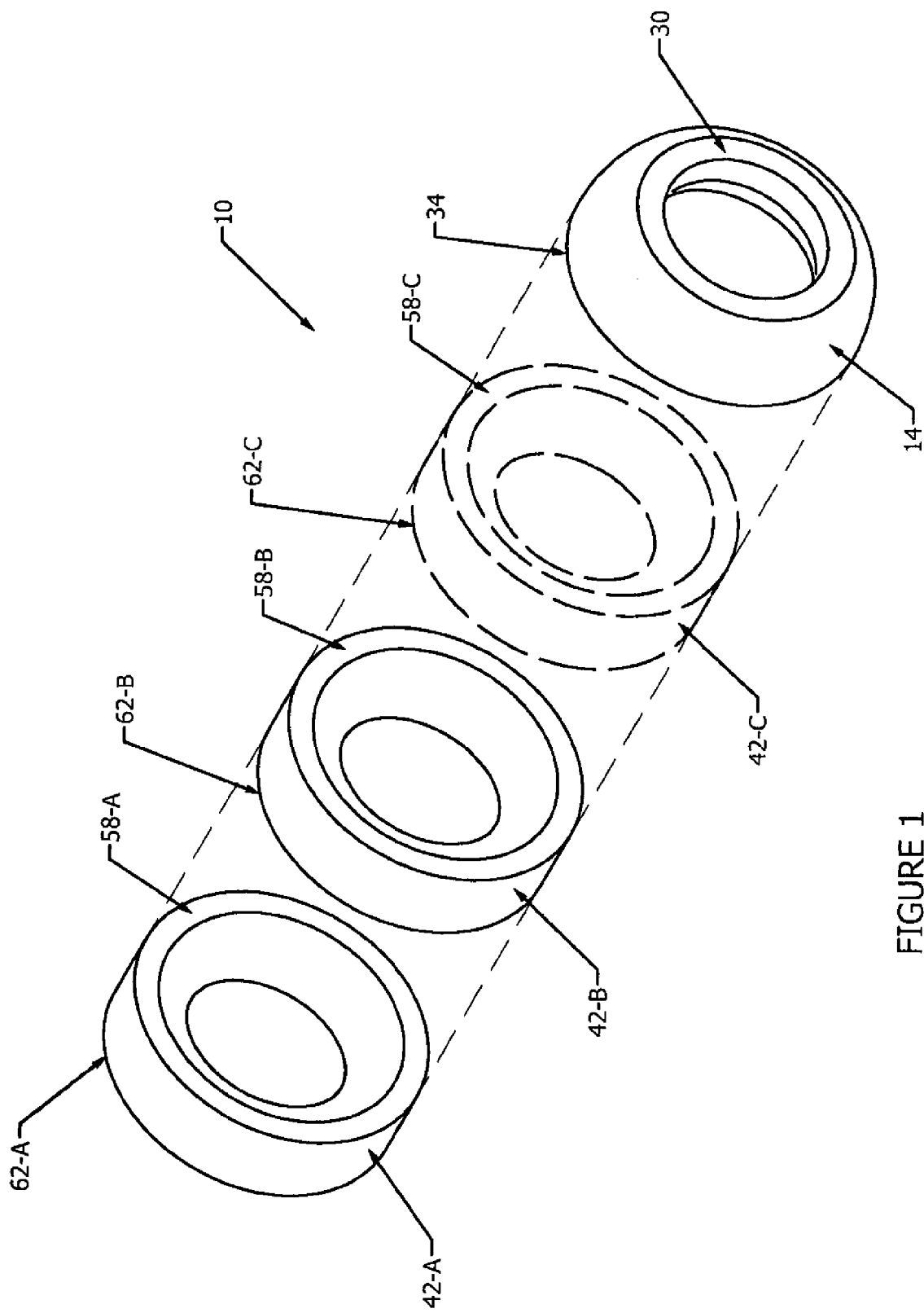
FIG. 1 illustrates an exploded perspective view of the penis enlargement device according to one exemplary embodiment of the present invention.
Figure 2:
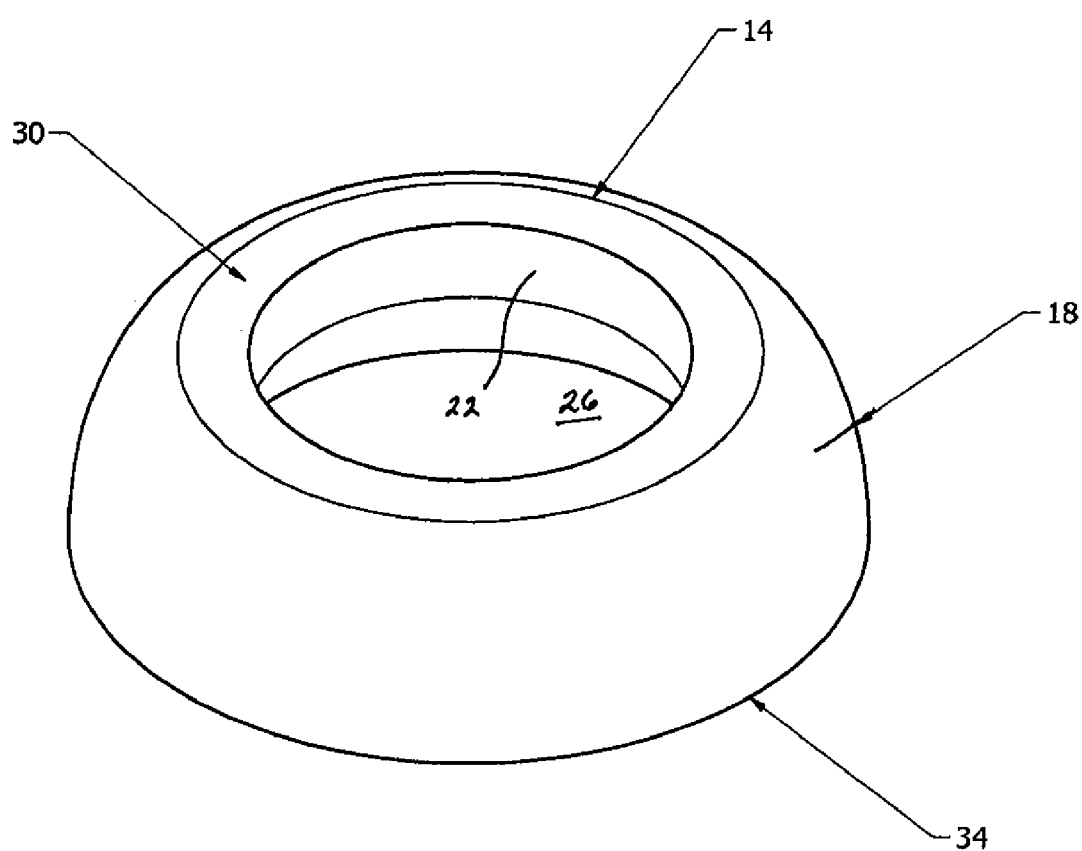
FIG. 2 illustrates a perspective view of the end ring of the penis enlargement device illustrated in FIG. 1.
Figure 3:
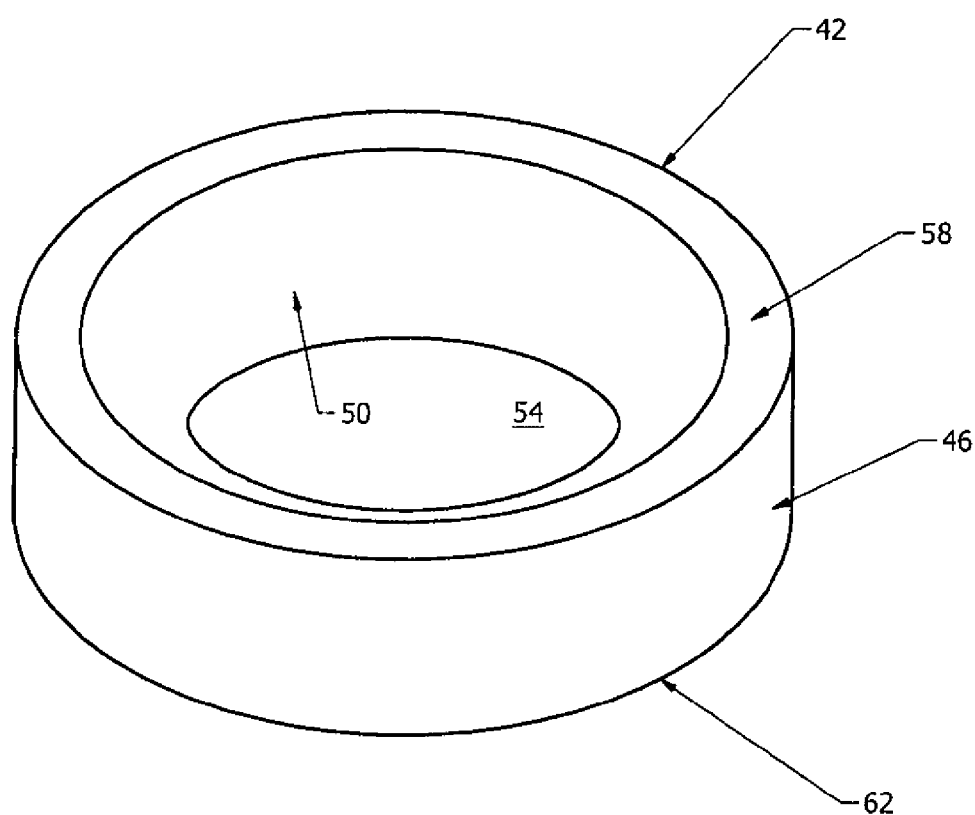
FIG. 3 illustrates a perspective view of the stealth ring of the penis enlargement device illustrated in FIG. 1.

With reference to FIG. 1, illustrated is a perspective view of the present invention penis enlargement device according to one exemplary embodiment. Specifically, FIG. 1 illustrates the penis enlargement device 10 as comprising an end ring 14 and a plurality of stealth rings 42, shown specifically as stealth rings 42-a, 42-b, and 42-c. The end ring 14 and each of the stealth rings 42 are sized and configured to be used with one another in an advantageous way to provide or make-up the penis enlargement device 10 as shown. Stated differently, the end ring 14 and the stealth rings 42 operate in concert with one another to form a penis enlargement device 10 that may vary in size and weight to achieve a desired end result. As will be discussed below, it will be apparent to one skilled in the art that the penis enlargement device 10 of the present invention may comprise a single ring, either the end ring 14 or a stealth ring 42, depending upon the desired penis enlargement activity or exercise to be undertaken and the results to be achieved. In addition, it will be obvious to one skilled in the art that the methods for enlarging the penis described herein and that are covered and that are to be practiced using the present invention penis enlargement device may be carried out using a single ring, or in the alternative a plurality of rings.

As is shown in the figures and as will be discussed in greater detail below, the end ring 14 is preferably configured slightly different than the stealth rings 42 in that it comprises a different shape and is configured to be positioned at the distal end of the penis, or near the head of the penis. Thus, the end ring 14, if used with one or more stealth rings 14, is designed to be placed on the penis after all other stealth rings 42 have been placed or positioned.

With reference to FIGS. 1, 2, 4, and 6, the end ring 14 is shown in the form of a cylinder with a thickness $t_1$ and having an outer sidewall 18 with a diameter $d_o$ and an inner sidewall 22 with a diameter $d_i$ to form a ring with an aperture 26 therethrough. The end ring 14 may be manufactured to comprise different or varying inside diameters $d_i$, as discussed below. Similarly, the end ring 14 may be manufactured to comprise different outside diameters $d_o$, also as described below. The aperture 26 and inner sidewall 22 of the end ring 14 are configured to receive the head and shaft of the penis. The end ring 14 slides onto the penis so that the inner sidewall 22, or at least a portion thereof, contacts and rests against the shaft of the penis where the end ring 14 may be positioned as needed. In most cases, the end ring 14 will be adjacent or proximate the head of the penis. The end ring 14 may be manufactured in different sizes, each having different inside diameters $d_i$ in order to accommodate different penis sizes.

The outer sidewall 18 of the end ring 14 is designed so that it transitions from a back mating edge 34 to a front edge 30 in an inwardly tapering manner. In the embodiment shown, the end ring 14 comprises a curved tapered outer sidewall 18, thus making the transition slightly more gradual. Specifically, the outer sidewall 18 tapers inwardly from the back mating edge 34 toward the inner sidewall 22 until it transitions into the front edge 30. Another way to describe the tapering outer sidewall 18 is to say that the outside diameter $d_o$ of the outer sidewall 18 varies, or is not constant.

The curved tapered outer sidewall 18 is advantageous in that it allows the wearer of the end ring 14 to be discreet while undergoing a penis enlargement session. This is particularly advantageous if the enlargement session is to be carried out in public. By curving the outer sidewall, the transition from sidewall to edge is dulled, thus enabling the wearer to wear the end ring 14 underneath clothing and reducing the likelihood that others will detect the presence of the end ring 14. Indeed, the tapered outer sidewall configuration of the end ring 14 provides the penis enlargement device 10 with a more natural looking design that makes its presence difficult to detect. The functionality of the present invention penis enlargement device is therefore increased as the user may undergo an enlargement session while participating in various everyday activities and with a reduced fear of embarrassment.

The inner sidewall 22 of the end ring 14 is designed so that it also transitions from a back mating edge 34 to a front edge 30. In some embodiments, the inner sidewall 22 is designed to comprise a constant or linear configuration. In other embodiments, the inner sidewall 22 is designed to comprise a nonlinear configuration, meaning that the inside diameter $d_i$ of the inner sidewall 22 varies or is not constant. Still in other embodiments, the inner sidewall 22 may be designed to comprise both a linear and a nonlinear configuration, meaning that it may comprise both a nonlinear segment and a linear segment, as viewed from a cross-sectional view, such as that shown in FIG. 6. As such, the present invention contemplates several different designs.

Those designs and configurations that are preferred and that are shown in the figures are those that comprise a linear or constant inside diameter segment of some length in combination with a nonlinear or variable inside diameter segment that extends away from the linear segment toward the outer sidewall 18 for the purpose of reducing the linear surface area in contact with the penis. In the embodiment shown in cross-section in FIG. 6, the inner sidewall 22 of the end ring 14 comprises a linear or constant inside diameter segment 23 that extends substantially perpendicular from the front edge 30 for a distance $x_3$ and that transitions into a nonlinear or variable inside diameter segment 25 that extends between the linear segment 23 and the back mating edge 34, and that expands away from the linear segment 23 toward the outer sidewall 18.

The linear or constant inside diameter segment is designed to be parallel to and rest against or contact the penis shaft and to support the end ring 14 on the penis when in use. The length or distance $x_3$ of the linear segment 23 may vary between differently manufactured end rings. In other words, different end ring designs are contemplated with linear segments of different length.

The nonlinear or variable inside diameter segment 25 facilitates easy placement of the end ring 14 over the head of the penis and onto the shaft as it provides for an aperture of increased size that initially interfaces with the penis. As the end ring 14 is placed over the head of the penis, the nonlinear segment 25 functions to guide the head of the penis into the narrower linear segment 23 of constant inside diameter. The nonlinear segment 25 further reduces the surface area of the inner sidewall 22 that is actually in contact with the skin of the penis by extending the surface of the inner sidewall 22 away from the penis. Extending at least a portion of the inner sidewall away from the penis functions to also reduce the chance of pinching the skin when the end ring 14 is used in conjunction with an adjacent stealth ring 42.

The end ring 14 further comprises a front edge 30 and a back mating edge 34, which are each preferably flat or planar in form, with surfaces that are substantially perpendicular to a central axis 38. The front edge 30 extends from the inner sidewall 22 to the outer sidewall 18 an comprises a width $x_1$ to form a surface configured to engage or interface with means for securing the end ring on the penis, which means for securing may comprise any type of device or structure known in the art, such as a wrap, a bandage, a strap, and others. The front edge is positioned so that its inside edge is adjacent and resting against the skin of the penis shaft. In this position, the front edge functions to reduce the likelihood that the wrap will become entrapped under or within the end ring 14.

The back mating edge 34, as the contact point between the end ring 14 and any adjacent stealth ring 42, extends from the inner sidewall 22 to the outer sidewall 18 and comprises a width $x_2$ to form a surface configured to receive a front mating edge of an adjacently placed stealth ring 42. Widths $x_1$ and $x_2$ may be the same or different, depending upon the desired configuration of the penis enlargement device 10. Unlike the front edge of the end ring, the back mating edge 34 is positioned near the outermost edge or circumference of the end ring 14 so that contact with a stealth ring occurs at significant distance above the skin of the penis shaft, thus reducing the chance for pinching when being applied and worn.

With reference to FIGS. 1, 3, 4, and 5, the stealth ring 42 is shown in the form of a cylinder with a thickness $t_2$ and having an outer sidewall 46 with a diameter $d_o$ and an inner sidewall 50 with a diameter $d_i$ to form a ring with an aperture 54 therethrough. The stealth ring 42 may be manufactured to comprise different or varying inside diameters $d_i$, as discussed below. Similarly, the stealth ring 42 may be manufactured to comprise different outside diameters $d_o$, also as described below. The aperture 54 and inner sidewall 50 of the stealth ring 42 are configured to receive the head and shaft of the penis. The stealth ring 42 slides onto the penis so that the inner sidewall 50, or at least a portion thereof, contacts and rests against the shaft of the penis where the stealth ring 42 may be positioned as needed. The stealth ring 42 may be manufactured in different sizes, each having different inside diameters $d_i$ in order to accommodate different penis sizes.

The outer sidewall 46 of the stealth ring 42 is designed so that it transitions from a back mating edge 62 to a front mating edge 58 in a substantially perpendicular manner. In the embodiment shown, the stealth ring 42 comprises a linear outer sidewall 18. The linear sidewall configuration is advantageous in that several stealth rings may be fitted together to appear as a homogeneous cylinder or tube, thus more closely resembling the penis. In essence, the linear outer sidewall 46 allows the wearer of one or more stealth rings 42 to be discreet while undergoing a penis enlargement session, particularly as these stealth rings 42 are worn in conjunction with the end ring 14 as shown in FIG. 1. Creating the look of a homogenous tube or cylinder is particularly advantageous if the enlargement session is to be carried out in public. The stealth rings allow the wearer to disguise the presence of the penis enlargement device 10, especially as hidden under the clothing of the wearer. Thus, the particular configuration of the stealth rings will reduce the likelihood that others will detect their presence, which will allow the wearer to perform several sessions at any time and in any place without the need to retreat to a private setting. Indeed, the linear configuration of the outer sidewalls of several stealth rings fitted together provides the penis enlargement device 10 with a more natural look that makes its presence difficult to detect. As indicated above, the functionality of the present invention penis enlargement device is increased as the user may undergo an enlargement session while participating in various everyday activities with reduced fear of embarrassment.

The inner sidewall 50 of the stealth ring 42 is designed so that it also transitions from a back mating edge 62 to a front mating edge 58. In some embodiments, the inner sidewall 50 is designed to comprise a constant or linear configuration, as viewed from a cross-sectional view. In other embodiments, the inner sidewall 50 is designed to comprise a nonlinear configuration, meaning that the inside diameter $d_i$ of the inner sidewall 50 varies or is not constant, such as the nonlinear configuration illustrated in FIG. 5. Still in other embodiments, the inner sidewall 50 may be designed to comprise both a linear and a nonlinear configuration, meaning that it may comprise both a nonlinear segment and a linear segment, as viewed from a cross-sectional view, such as that also illustrated in FIG. 5, wherein a linear segment is represented by the dotted lines. As such, the present invention contemplates several different designs.

Those designs and configurations that are preferred and that are shown in the figures are those that comprise a nonlinear or variable inside diameter configuration that extends away from the smallest inside diameter measurement, or away from the central axis 38, toward the outer sidewall 46 for the purpose of reducing the surface area in contact with the penis. In the embodiment shown in cross-section in FIG. 5, the inner sidewall 50 of the stealth ring 42 comprises continuously curved convex configuration that extends between the front mating edge 58 and the back mating edge 62.

Similar to the end ring 14, the nonlinear or variable inside diameter configuration of the stealth ring 42 facilitates easy placement over the head of the penis and onto the shaft as it provides for an aperture of increased size that initially interfaces with the penis. As the stealth ring 42 is placed over the head of the penis, the nonlinear configuration functions to guide the head of the penis into the narrower diameter segment, shown as diameter $d_i$ in FIG. 4. The nonlinear configuration further reduces the surface area of the inner sidewall 50 that is actually in contact with the skin of the penis by extending the surface of the inner sidewall 50 away from surface of the penis. Extending at least a portion of the inner sidewall 50 away from the penis functions to also reduce the chance of pinching the skin when one stealth ring is brought into contact with another stealth rings or with an end ring, as is discussed below.

The stealth ring 42 further comprises a front mating edge 58 and a back mating edge 62, which are each preferably flat or planar in form, with surfaces that are substantially perpendicular to a central axis 38. These front and back mating edges 58 and 62 function as the contact points or surfaces for adjacent stealth rings and/or an end ring. Specifically, the front mating edge 58 extends from the inner sidewall 50 to the outer sidewall 46 and comprises a width $x_2$ to form a surface configured to engage or mate with the back mating edge of an adjacent stealth ring or the back mating edge 34 of an adjacent end ring 14. The back mating edge 62 extends from the inner sidewall 50 to the outer sidewall 46 and comprises a width $x_2$ to form a surface configured to receive a front mating edge of an adjacent stealth ring 42. Widths $x_2$ of the stealth ring 42 may be the same or different, depending upon the desired configuration of the penis enlargement device 10. In addition, the front and back mating edges 58 and 62 are positioned near the outermost edge or circumference of the stealth ring 42 so that contact with an adjacent stealth ring or an end ring occurs at a significant distance above the skin of the penis shaft, thus reducing the chance for pinching when being applied and worn.

The penis enlargement device 10 may comprise a single ring or a plurality of rings as they are described herein. If a single ring is employed, it may be the end ring 14 or a stealth ring 42. However, the stealth rings 42 are particularly designed for use with the end ring 14 and thus a user wanting to wear only a single ring would most likely wear the end ring 14 because of its tapering outer sidewall design. If a plurality of rings are employed, the end ring 14 will typically be used with one or more stealth rings 42.

Figure 4:
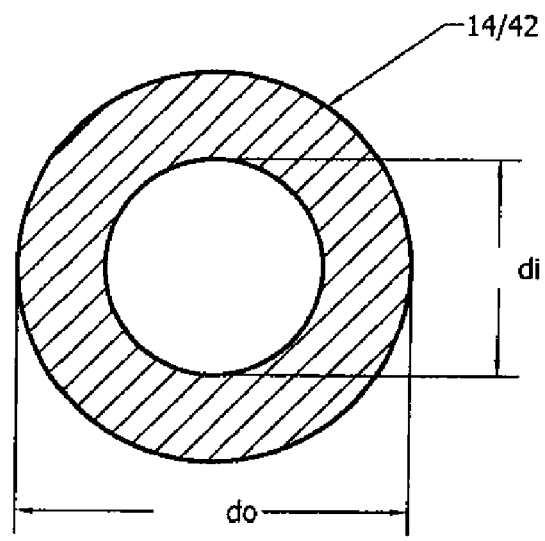
FIG. 4 illustrates a top view of either the end ring or the stealth ring of the penis enlargement device of FIG. 1 showing common dimensions.
Figure 5:
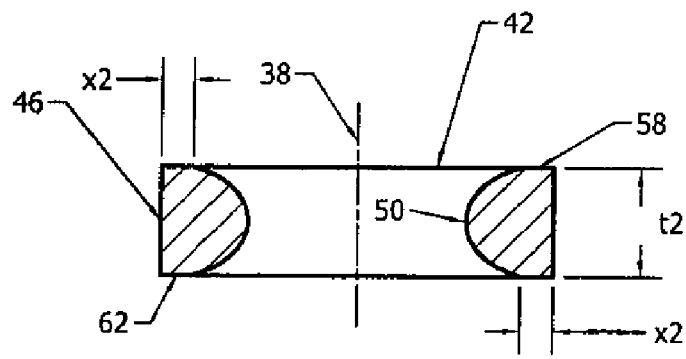
FIG. 5 illustrates a cut-away side view of the stealth ring of the of the penis enlargement device of FIG. 1.
Figure 6:
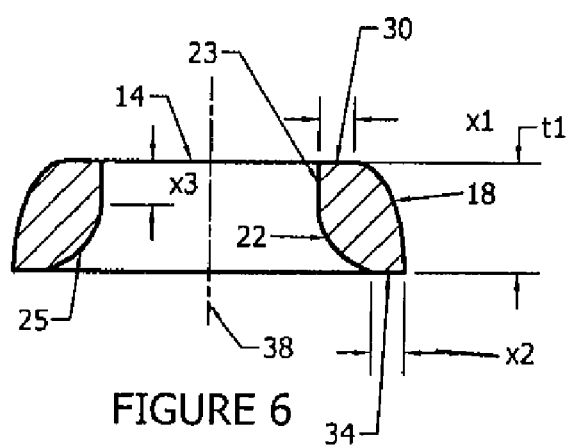
FIG. 6 illustrates a cut-away side view of the end ring of the penis enlargement device of FIG. 1.

It is noted and shown in FIG. 4, that end ring 14 and stealth ring(s) 42 preferably share a common inside diameter $d_i$, as well as a common outside diameter $d_o$. Specifically, the common inside diameter $d_i$ shared between end ring 14 and stealth ring(s) 42 is that diameter that is actually in contact with the penis. End ring 14 and stealth ring(s) 42 preferably share a common outer diameter $d_o$ in order to be congruent and produce a homogeneous shaft to resemble the penis as closely as possible and to enable the wearer to be as discreet as possible. Despite the presence of nonlinear segments in either of the inner or outer sidewalls, there is preferably at least a portion of these sidewalls that share a common diameter for the reasons given above.

Figure 7:
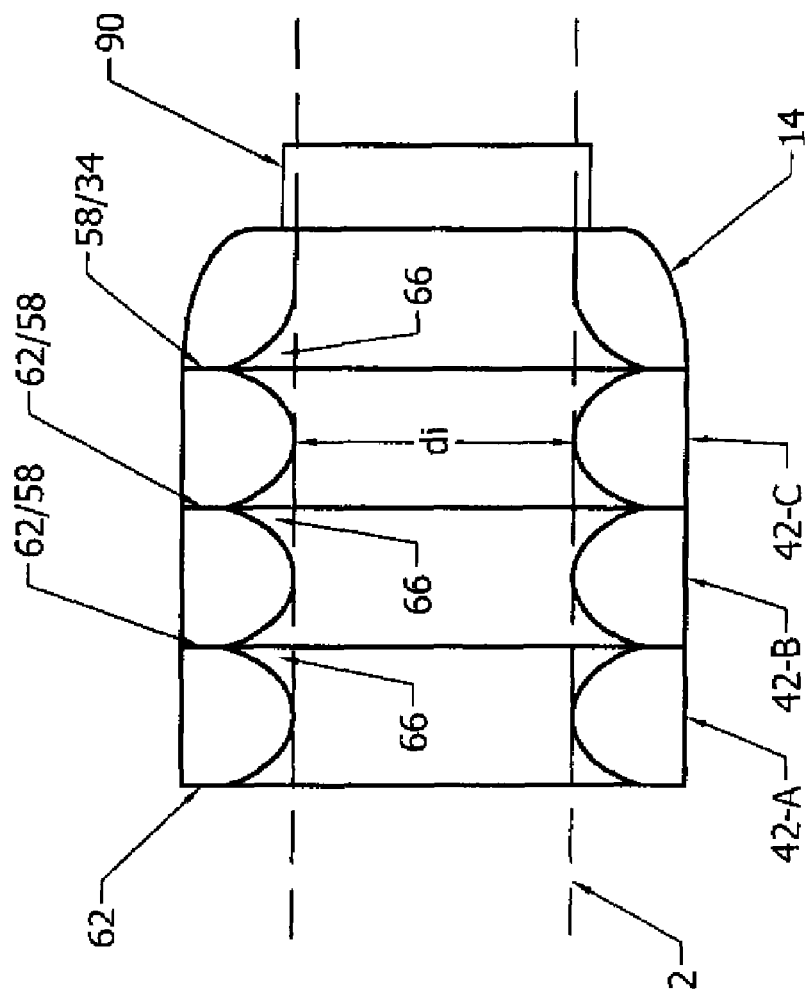
FIG. 7 illustrates a cut-away side view of two juxtaposed rings.

Referring now to FIG. 7, illustrated is a cut-away side view of several juxtaposed rings, namely stealth rings 42-a, 42-b, 42-c, and end ring 14, as inserted onto and positioned about the shaft 2 of a penis with means for securing in place to secure the end ring 14, as well as the stealth rings 42, in place, with means for securing shown in the form of a flexible wrap 90. As shown, the positioning of the stealth rings 42-a, 42-b, and 42-c adjacent one another causes the front and back mating edges 58 and 62, respectively, of these rings to be in contact. Similarly, the positioning of the end ring 14 adjacent stealth ring 42-c causes the front mating edge 58 of the stealth ring 42-c to be in contact with the back mating edge 34 of the end ring 14. In this correct position, a gap or volume of space 66 is formed or created, which volume of space 66 forms as a result of the nonlinear configuration of the inside sidewalls of the various rings. The creation of this volume of space 66 provides one of the more significant advantages of the present invention. As indicated, the end ring 14 and each of the stealth rings 42 are designed to be placed and worn in contact with one another over the shaft 2 of the penis in order to achieve the look of a homogeneous cylinder. This cylinder may comprise an overall length equivalent to the cumulative thicknesses t of each ring worn, which length may be similar to the natural length of the penis, thus allowing the user to discreetly wear the penis enlargement device. By providing rings with a nonlinear inner sidewall and extending a portion of this inner sidewall away from narrowest inside diameter segment $d_i$ and the skin of the penis, the volume of space 66 is formed as the rings are brought into contact with one another. This volume of space 66 is configured to receive a portion of skin in the event the skin is displaced by the positioning of the rings onto the shaft 2. however, the volume of space 66 created is such that a significant amount of skin would be required to displace in order to pinch the skin between two adjacently placed rings. In effect, the nonlinear configuration of the inner sidewalls and the extension of a portion of the inner sidewalls away from the narrowest inside diameter segment $d_i$ that is in contact with the shaft 2 of the penis, functions to position the mating edges 34, 52, and 62 of the end and stealth rings 14 and 42, which mating edges are linear and which do comprise edges capable of pinching the skin, above or away from the skin surface of the penis shaft 2. As such, the likelihood that these mating edges will pinch the skin as two rings are brought in contact with one another is significantly reduced.

Figure 8:
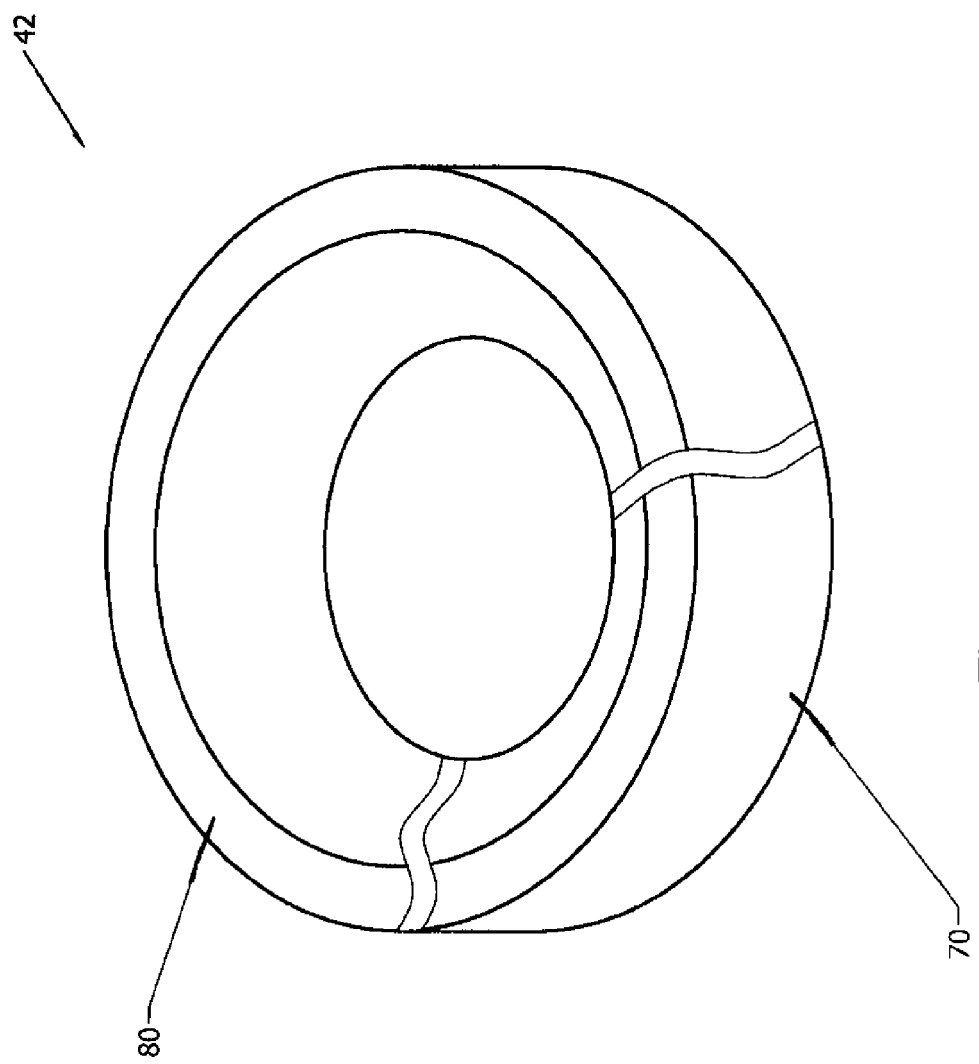
FIG. 8, illustrates a perspective view of a stealth ring having a part of its structure cut-away for illustration of the various weighted mass and protective covering components, according to one exemplary embodiment of the present invention.

Each of the end rings and the stealth rings further comprise a pre-determined mass or weight in order to provide a tensioning or hanging effect when placed or worn on the penis. Referring to FIG. 8, shown is stealth ring 42 having a part of its structure cut-away for illustration purposes. Specifically, FIG. 8 illustrates stealth ring 42 as comprising a weighted mass 70. As will be recognized by one skilled in the art, weighted mass 70 may comprise any weight sufficient to tension or stretch the penis. The weighted mass 70 preferably comprises a lead material make-up. However, weighted mass 70 my be comprised of other materials suitable to tension and stretch the penis, such as stainless steel or any other material comprising sufficient weight. In one exemplary embodiment, the weighted mass of the end ring and the stealth rings of the penis enlargement device are comprised of lead weighing approximately 10 oz. each. Thus, if a single end ring is used in a penis enlargement session, the penis will be subject to a 10 oz. weight that will provide minimal stretching of the ligaments, skin, and other physiological structures of the penis. If an end ring is worn in conjunction with one or more stealth rings, the weight increases in increments of 10 oz depending upon the number of stealth rings worn or used in conjunction with the end ring. In essence, depending upon the desired weight to be applied to the penis, and depending upon the desired amount of stretch of the penis, the wearer simply places additional rings onto the penis to increase the overall weight.

The weight of the end ring and the stealth rings will most likely be the same. However, it is contemplated that the end ring may comprise a different weight than the stealth rings, or that the stealth rings themselves may comprise different weights. For example, it may be desirous to use a light weight end ring with heavier stealth rings, or vice versa, which may provide more comfort for the wearer. As such, several different categories of rings may be manufactured that the wearer may select from for any given penis enlargement session with the idea that not every penis enlargement session should have to be the same. For instance, the wearer may want to apply relatively heavy weights to his penis during a morning or evening enlargement session. This can be done by selecting the appropriate end ring and stealth rings, each having a pre-determined weight, from a selection of rings. On the other hand, the wearer may want to apply relatively light weights to his penis to enable him to carry out an extended penis enlargement session throughout the day. In this instance, the user may select an end ring that is around 6 oz. with one or more stealth rings also weighing around 6 oz. Or, the wearer may select to wear only one or two rings weighing 10 oz. each. Either way, the wearer has the ability to vary the weight between penis enlargement sessions by selecting the number of individual rings to be used, and also the weights of the individual rings to be used. Enabling the user to selectively and specifically control the penis enlargement session using the present invention penis enlargement device in this manner increases the satisfaction, results, and safety of penis enlargement, especially over prolonged periods of time, which is typically required for satisfactory results. Indeed, satisfaction is increased because each wearer may customize each penis enlargement session as needed. This is particularly advantageous as not every individual is the same, with the same needs or desired end results. Results are increased because the wearer can cater each enlargement session to present circumstances and/or comfort levels. As prolonged stretching of the penis is required to achieve satisfactory results, the present invention penis enlargement device allows the wearer to wear one or more rings for extended periods of time, even in public under clothing. Also, the wearer can vary the overall weight applied to the penis from session to session by selectively altering the penis enlargement device, thus catering to present comfort levels. Finally, safety is increased because the penis may be stretched under different weights from session to session. While heavy weights may provide quick results, it may not be safe to subject the penis to such a load for more than a short time. However, wearers realize that prolonged use is required in order to achieve satisfactory results. The present invention allows the wearer relieve the penis of heavy weights, yet still apply minimal amounts of weight to maintain the enlargement session for a prolonged period of time.

FIG. 8 also illustrates stealth ring 42 as comprising a protective outer covering 80. Protective covering 80 is configured to encase the weighted mass structure 70 and to provide a more comfortable feel to the rings of the penis enlargement device. Protective covering 80 may be comprised of any known material in the art, but will typically comprise rubber, plastic, nylon, or any other suitable material.

Referring back to FIG. 1, the present invention penis enlargement device will typically comprises an end ring and one or more stealth rings. In the embodiment shown, the penis enlargement device 10 comprises a single end ring 14 and two stealth rings, namely stealth rings 42-a and 42-b. Other stealth rings may be added, as indicated by the stealth ring 42-c illustrated in phantom view. To participate in a penis enlargement session, each of these rings are inserted over the head of the penis and are brought to rest and positioned about the penis shaft. The order of placement is not critical, but will typically include placement and positioning of the stealth rings 42 first, followed by placement and positioning of the end ring 14, which is brought to rest proximate the head of the penis. Together, the stealth rings 42 and the end ring 14 are configured to stretch or tension the penis. Stated differently, the stealth rings 42 and the end ring 14, as weighted structures, induce or apply a downward force to the penis caused by the weight of the rings under gravity. This downward force functions to stretch the ligaments and other physiological structures of the penis. If stretched over a sufficient period of time, the penis is caused to permanently lengthen, thus enlarging the penis. The penis enlargement device may be worn for random or pre-determined periods of time.

As thus described, the present invention penis enlargement device solves many of the problems inherent in prior related devices or systems. First, the nonlinear inner sidewall configuration causes the contact points (e.g., the mating edges or surfaces) of the one or more juxtaposed rings to be kept away from the shaft and skin of the penis. Second, the cumulative effect of several rings juxtaposed to one another about the shaft of the penis is to create the look of a homogeneous cylinder or tube, thus allowing the wearer to disguise the presence of the device. Third, the rings are comprised of a weighted material, such as lead, that is encapsulated or encased inside a tough protective covering, such as rubber or plastic, which provides added comfort while housing significant weight in a small volume. Fourth, the end ring comprises a front surface or edge configured to interface with some type of means for securing the end ring and any stealth rings on the shaft of the penis. This surface or edge provides an interface feature for the means for securing that precludes entrapment of the means, thus considerably extending wear times. Fifth, the end ring comprises a tapering outer sidewall, thus allowing the user to disguise the presence of the device even more. The combination of the features of the present invention penis enlargement device allows the user to discreetly wear the device even in public environments without the fear of someone noticing the device and embarrassing the wearer. Other advantages not specifically recited herein will be apparent to those skilled in the art. As such, those recited should not be construed as limiting in any way.

The foregoing detailed description describes the invention with reference to specific exemplary embodiments. However, it will be appreciated that various modifications and changes can be made without departing from the scope of the present invention as set forth in the appended claims. The detailed description and accompanying drawings are to be regarded as merely illustrative, rather than as restrictive, and all such modifications or changes, if any, are intended to fall within the scope of the present invention as described and set forth herein.

More specifically, while illustrative exemplary embodiments of the invention have been described herein, the present invention is not limited to these embodiments, but includes any and all embodiments having modifications, omissions, combinations (e.g., of aspects across various embodiments), adaptations and/or alterations as would be appreciated by those in the art based on the foregoing detailed description. The limitations in the claims are to be interpreted broadly based the language employed in the claims and not limited to examples described in the foregoing detailed description or during the prosecution of the application, which examples are to be construed as non-exclusive. For example, in the present disclosure, the term "preferably" is non-exclusive where it is intended to mean "preferably, but not limited to." Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; b) a corresponding function is expressly recited; and c) structure, material or acts that support that structure are expressly recited. Accordingly, the scope of the invention should be determined solely by the appended claims and their legal equivalents, rather than by the descriptions and examples given above.

The invention claimed is:

1. A penis enlargement device comprising:
   an end ring configured to be inserted onto a shaft of a penis and to be positioned proximate a head of said penis, said end ring comprising a weighted mass to effectuate stretching of said penis, and a non-uniform outside diameter to facilitate concealment thereof when being worn;
   a stealth ring also configured to be inserted onto said shaft of said penis to be positioned aft of and adjacent said end ring, said end ring and said stealth ring forming a stealth configuration,
   said end ring and said stealth ring forming a volume of space therebetween upon being positioned adjacent one another, said volume of space being configured to receive the skin of said penis, thereby reducing the likelihood of pinching said skin upon positioning said end and stealth rings about said shaft of said penis.

2. The penis enlargement device of claim 1, wherein said end ring comprises a front edge, a back edge, an outer sidewall extending between said front and back edges, and an inner sidewall also extending between said front and back edges.

3. The penis enlargement device of claim 2, wherein said inner sidewall of said end ring comprises, at least in part, a nonlinear variable diameter segment configured to position said back edge above said shaft and to define a portion of said volume of space.

4. The penis enlargement device of claim 2, wherein said stealth ring comprises a front edge configured to interface with said back edge of said end ring or a second stealth ring adjacent thereto, a back edge configured to interface with a second stealth ring, an outer sidewall extending between said front and back edges, and an inner sidewall also extending between said front and back edges.

5. The penis enlargement device of claim 4, wherein said inner sidewall of said stealth ring comprises, at least in part, a nonlinear variable diameter configured to locate said front and back edges proximate said outer sidewall and above said shaft and to define a portion of said volume of space.

6. The penis enlargement device of claim 1, wherein said stealth ring comprises a weighted mass to assist said end ring in stretching said penis and to increase the overall load borne by said penis.

7. The penis enlargement device of claim 1, further comprising means for securing said end ring and said penis enlargement device in position on said shaft of a penis.

8. The penis enlargement device of claim 1, wherein said stealth ring comprises a linear outer sidewall, such that when positioned adjacent said end ring and/or adjacent a second stealth ring, said penis enlargement device will comprise a look of a homogeneous cylinder to disguise the presence of said penis enlargement device when being worn.

9. A penis enlargement device comprising:
    an end ring configured to be inserted onto a shaft of a penis and to be positioned proximate a head of said penis, said end ring comprising a weighted mass, a front edge configured to be located against said shaft, a back edge supported above said shaft by an inner sidewall extending between said front edge and said back edge, said inner sidewall having, at least in part, a nonlinear variable diameter segment, and an outer sidewall extending between said front edge and said back edge; and
    a first stealth ring also configured to be inserted onto said shaft of said penis adjacent said end ring, said end ring and said stealth ring forming a stealth configuration, said stealth ring comprising a weighted mass, a front edge configured to interface with said back edge of said end ring, a back edge configured to interface with a second stealth ring, an outer sidewall extending between said front and back edges, and an inner sidewall also extending between said front and back edges and having, at least in part, a nonlinear variable diameter configured to locate said front and back edges proximate said outer sidewall and above said shaft, said inner sidewall of said end ring and said inner sidewall of said stealth ring defining a volume of space capable of receiving the skin of said shaft of said penis to reduce the likelihood of pinching upon positioning said stealth ring adjacent said end ring.

10. The penis enlargement device of claim 9, further comprising a second stealth ring configured to be inserted onto said shaft of said penis adjacent said first stealth ring, said second stealth ring comprising a weighted mass, a front edge configured to interface with said back edge of said first stealth ring, a back edge configured to interface with a third stealth ring, an outer sidewall extending between said front and back edges, and an inner sidewall also extending between said front and back edges and having, at least in part, a nonlinear variable diameter configured to locate said front and back edges proximate said outer sidewall and above said shaft, said inner sidewall of said first stealth ring and said inner sidewall of said second stealth ring defining a volume of space capable of receiving the skin of said shaft of said penis to reduce the likelihood of pinching upon positioning said first stealth ring adjacent said second stealth ring.

11. A method for enlarging a penis of a human male, said method comprising:
    inserting an end ring onto a shaft of said penis, said end ring comprising a weighted mass, a front edge, a back edge, an outer sidewall extending between said back and front edges in an inwardly tapering manner to help conceal said end ring, and an inner sidewall also extending between said front and back edges;
    positioning said end ring proximate a head of said penis, said end ring being configured to stretch said penis;
    securing said end ring in position on said shaft of said penis;
    inserting at least one stealth ring onto said shaft of said penis prior to said inserting said end ring, said stealth ring being configured to facilitate its concealment when being worn; and
    wearing said end ring periodically for a duration of time to effectuate enlargement of said penis.

12. The method of claim 11, further comprising positioning said stealth ring adjacent said end ring.

13. The method of claim 11, wherein said stealth ring comprises a front edge configured to interface with said back edge of said end ring or an adjacent stealth ring, a back edge configured to interface with an adjacent stealth ring, an outer sidewall extending between said front and back edges, and an inner sidewall also extending between said front and back edges.

14. The method of claim 11, wherein said stealth ring comprises a weighted mass to assist said end ring in stretching said penis and to increase the overall load borne by said penis.

15. The method of claim 11, wherein said stealth ring comprises, at least in part, a nonlinear variable diameter configured to locate said front and back edges proximate said outer sidewall and above said shaft.

16. The method of claim 11, wherein said inner sidewall has, at least in part, a nonlinear variable diameter segment configured to position said back edge above said shaft of said penis.

* * * * *